(12) United States Patent
de Waele

(10) Patent No.: US 10,580,175 B2
(45) Date of Patent: Mar. 3, 2020

(54) APPARATUS, METHOD AND SYSTEM FOR RESOLUTION DEPENDENT GRAPHICAL REPRESENTATION OF SIGNALS

(71) Applicant: KONINKLIJKE PHILIPS N.V., Eindhoven (NL)

(72) Inventor: Stijn de Waele, Millwood, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/550,414

(22) PCT Filed: Feb. 19, 2016

(86) PCT No.: PCT/IB2016/050892
§ 371 (c)(1),
(2) Date: Aug. 11, 2017

(87) PCT Pub. No.: WO2016/135597
PCT Pub. Date: Sep. 1, 2016

(65) Prior Publication Data
US 2018/0033169 A1 Feb. 1, 2018

Related U.S. Application Data

(60) Provisional application No. 62/120,398, filed on Feb. 25, 2015.

(51) Int. Cl.
*G06T 11/20* (2006.01)
*G06F 3/0487* (2013.01)
(Continued)

(52) U.S. Cl.
CPC .......... *G06T 11/206* (2013.01); *G06F 3/0487* (2013.01); *G06T 11/60* (2013.01);
(Continued)

(58) Field of Classification Search
CPC combination set(s) only.
See application file for complete search history.

(56) References Cited

U.S. PATENT DOCUMENTS 5,608,861 A * 3/1997 Mead ............... G06T 11/206
715/700
5,724,032 A 3/1998 Klein et al.
(Continued)

FOREIGN PATENT DOCUMENTS

JP H11108702 A 4/1999
WO 2009139970 A2 11/2009
(Continued)

*Primary Examiner* — Motilewa Good Johnson

(57) ABSTRACT

A system, method and non-transitory computer-readable storage medium used to control the display of a display device. Controlling of the display device includes receiving data including a plurality of data points, each of the data points including a value along a first axis and a value along a second axis, dividing the data into a plurality of bins along the first axis, wherein the data is divided based on a physical attribute of the display device, determining, for one of the bins, whether an alternative data representation should be used, and displaying a plot of the data, wherein the alternative data representation is used for the one of the bins when it is determined that the alternative data representation should be used, wherein line plotting is used for the one of the bins when it is determined that the alternative data representation should not be used.

14 Claims, 4 Drawing Sheets

(51) Int. Cl.
  *G06T 11/60* (2006.01)
  *G16H 40/63* (2018.01)
  *A61B 5/024* (2006.01)
  *G06T 1/20* (2006.01)

(52) U.S. Cl.
  CPC ......... *A61B 5/024* (2013.01); *A61B 2576/023* (2013.01); *G06T 1/20* (2013.01); *G16H 40/63* (2018.01)

(56) References Cited

U.S. PATENT DOCUMENTS

| | | | |
|---|---|---|---|
| 5,801,688 A | 9/1998 | Mead et al. | |
| 7,756,676 B1* | 7/2010 | Shan | G06F 17/30551 |
| | | | 702/182 |
| 2006/0142948 A1* | 6/2006 | Minor | G16B 25/00 |
| | | | 702/19 |
| 2008/0036767 A1 | 2/2008 | Janzen | |
| 2010/0016215 A1 | 1/2010 | Moulton et al. | |
| 2010/0188406 A1* | 7/2010 | Kincaid | G01R 1/025 |
| | | | 345/440 |
| 2011/0169835 A1* | 7/2011 | Cardno | G06Q 10/06 |
| | | | 345/440 |
| 2012/0259583 A1* | 10/2012 | Noboa | G05B 15/02 |
| | | | 702/179 |
| 2012/0313949 A1* | 12/2012 | Rope | G06T 11/206 |
| | | | 345/440 |
| 2013/0019196 A1 | 1/2013 | Bhatt | |
| 2013/0103320 A1* | 4/2013 | Dzakula | C12Q 1/6879 |
| | | | 702/19 |
| 2013/0142381 A1* | 6/2013 | Field | G01J 3/28 |
| | | | 382/100 |
| 2015/0379110 A1* | 12/2015 | Marvasti | G05B 23/0227 |
| | | | 707/740 |
| 2016/0005198 A1* | 1/2016 | Penumatcha | G05B 23/0232 |
| | | | 345/589 |
| 2016/0093073 A1* | 3/2016 | Siegel | G06T 11/206 |
| | | | 345/589 |

FOREIGN PATENT DOCUMENTS

| | | |
|---|---|---|
| WO | 2012084176 A2 | 6/2012 |
| WO | 2012140264 A2 | 10/2012 |
| WO | 2014203088 A1 | 12/2014 |

* cited by examiner

_US 10,580,175 B2_

APPARATUS, METHOD AND SYSTEM FOR RESOLUTION DEPENDENT GRAPHICAL REPRESENTATION OF SIGNALS

CROSS-REFERENCE TO PRIOR APPLICATIONS

This application is the U.S. National Phase application under 35 U.S.C. § 371 of International Application No. PCT/IB2016/050892, filed on Feb. 19, 2016, which claims the benefit of U.S. Provisional Application Ser. No. 62/120,398, filed Feb. 25, 2015. These applications are hereby incorporated by reference herein, for all purposes.

A standard approach to plotting signals is to use linear interpolation to draw a line between a point representing each individual sample in the signal. This approach may provide a useful and readable display when the number of samples is small. However, as the number of samples grows to become significantly greater than the number of pixel columns of a display used to provide the plot to a user, the display may become cluttered.

A non-transitory computer-readable storage medium storing a set of instructions that are executable by a processor. The set of instructions, when executed by the processor, causing the processor to perform operations including receiving data including a plurality of data points, each of the data points including a value along a first axis and a value along a second axis, dividing the data into a plurality of bins along the first axis, wherein the data is divided based on a physical attribute of a display device on which the data is to be displayed, determining, for one of the bins, whether an alternative data representation should be used, and displaying a plot of the data, wherein the alternative data representation is used for the one of the bins when it is determined that the alternative data representation should be used, wherein line plotting is used for the one of the bins when it is determined that the alternative data representation should not be used.

A system having a data interface receiving data including a plurality of data points, each of the data points including a value along a first axis and a value along a second axis, a display device, a non-transitory memory storing a set of instructions and a processor executing the set of instructions. Executing the instructions causes the processor to perform operations including dividing the data into a plurality of bins along the first axis, wherein the data is divided based on a physical attribute of the display device, determining, for one of the bins, whether an alternative data representation should be used, displaying, using the display device, a plot of the sample of data, wherein the alternative data representation is used for the one of the bins when it is determined that the alternative data representation should be used, wherein line plotting is used for the one of the bins when it is determined that the alternative data representation should not be used.

A method for controlling a display device. The method including receiving data including a plurality of data points, each of the data points including a value along a first axis and a value along a second axis, determining whether the data points are to be displayed using a first data representation or a second data representation, wherein the determining is based on a physical attribute of the display device and displaying a plot of the data wherein a histogram representation of at least some of the data points is displayed when it is determined the first data representation is to be used, and second type of representation of at least some of the data points is displayed when it is determined the second data representation is to be used.

Figure 1:
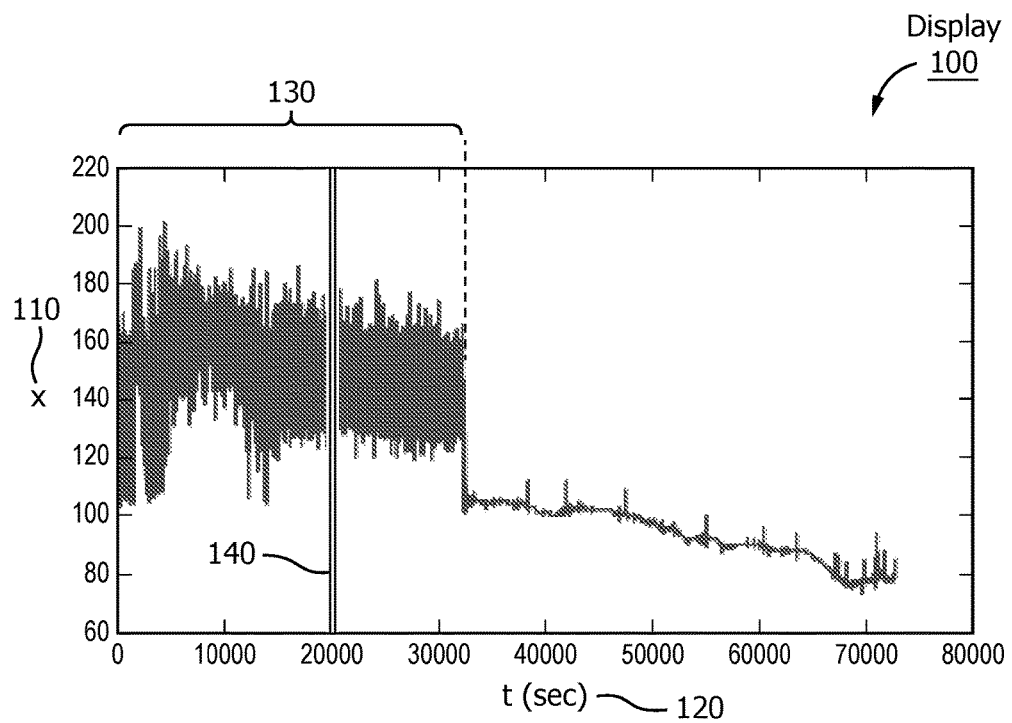
FIG. 1 shows a data sample plotted using standard linear interpolation.

The exemplary embodiments may be further understood with reference to the following description and the related appended drawings, wherein like elements are provided with the same reference numerals. Specifically, the exemplary embodiments relate to methods and systems for improving the amount of information conveyed in a graphical displays through the use of histograms.

A signal may be defined as a value x as a function of time t. The number of samples in the signal may be denoted N. A plot displaying a signal may typically display each sample in chronological order, with the sample times t along the x-axis and the sample values x along the y-axis. The signal may typically be shown with samples connected by a line. In many applications, such as heart rate monitoring of a patient, a large number of samples (e.g., $N>10^4$) may be shown in a single display. For example, a display showing one day of data sampled at 1 Hz includes $8.64*10^4$ samples.

However, in the display of a signal with a large number of samples, each column of pixels (or "pixel column") on a screen will include a large number of samples. For example, a high-definition display may be 1920 pixels in width; thus, if one day of data sampled at 1 Hz is shown on such a display, each pixel column will include $8.64*10^4/1920=45$ samples. This results in a cluttered and unreadable display. FIG. 1 illustrates such a display 100, with heart rate 110 plotted over time 120. In the display 100, it may be difficult to glean useful data from the first portion 130 due to the large number of data points. This difficulty will be even greater for lower-definition displays that are fewer pixels in width.

Figure 2:
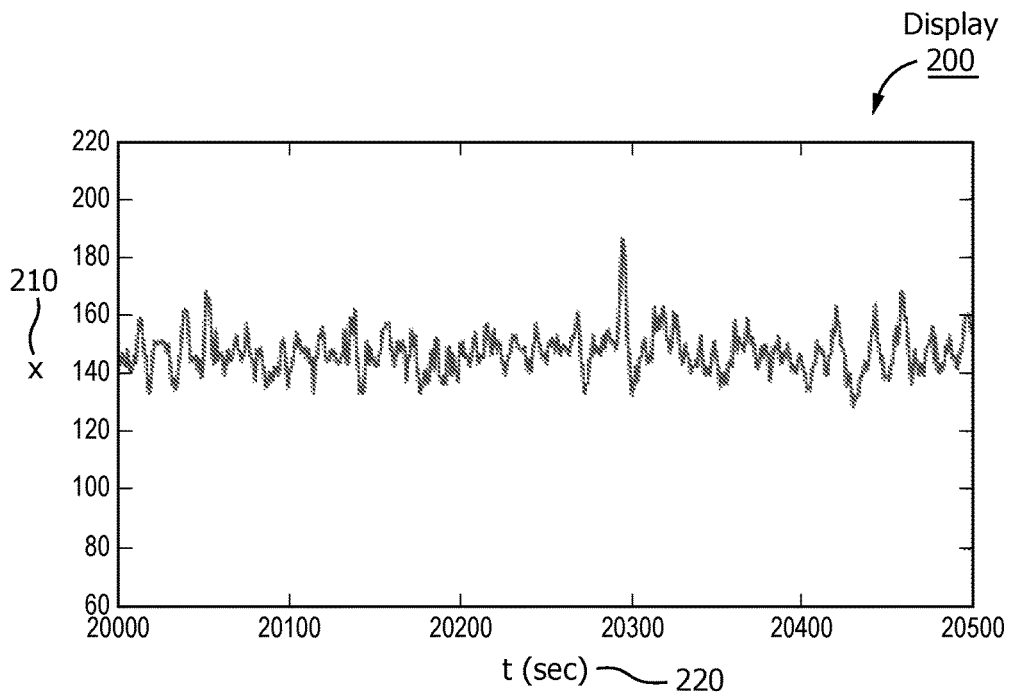
FIG. 2 shows a zoomed view of a portion of the sample shown in FIG. 1.

One common technique that may be used to gain greater insight into the contents of a signal plot is zooming in on a selected time interval, such as time interval 140 of FIG. 1. FIG. 2 illustrates a display 200 with heart rate 210 plotted over time 220, with the interval of time 220 corresponding to time interval 140 of FIG. 1. The linear interpolation between the various samples shown in the display 200 is much clearer than in first portion 130 of display 100. This is the case because interpolation across several pixel columns leads to a more clear display. Linear interpolation in general and linear interpolation across several pixel columns may be generally referred to as "line plotting." It should be noted that line plotting may also cover other types of rendering. However, it will be apparent to those of skill in the art that the zoomed view of display 200 does not provide proper context within the overview of display 100 and in some cases (e.g., when there are a large number of data points), it is not possible to interpolate across several pixel columns.

The exemplary embodiments provide alternative techniques for displaying dense signal plots having a large number of samples in each pixel column through the selective use of histograms. The exemplary embodiments will be described with specific reference to the signal shown in FIG. 1, but it will be apparent to those of skill in the art that this is only exemplary. It should be noted that a system implementing the exemplary embodiments may select among various rendering methods. For example, the rendering method may be selected based on the level of a complete signal, depending on the zoom level. When the level is zoomed out, meaning more pixels per column, the exemplary system may switch to a histogram representation. When the level is zoomed in, the exemplary system may switch to interpolation rendering.

Figure 3:
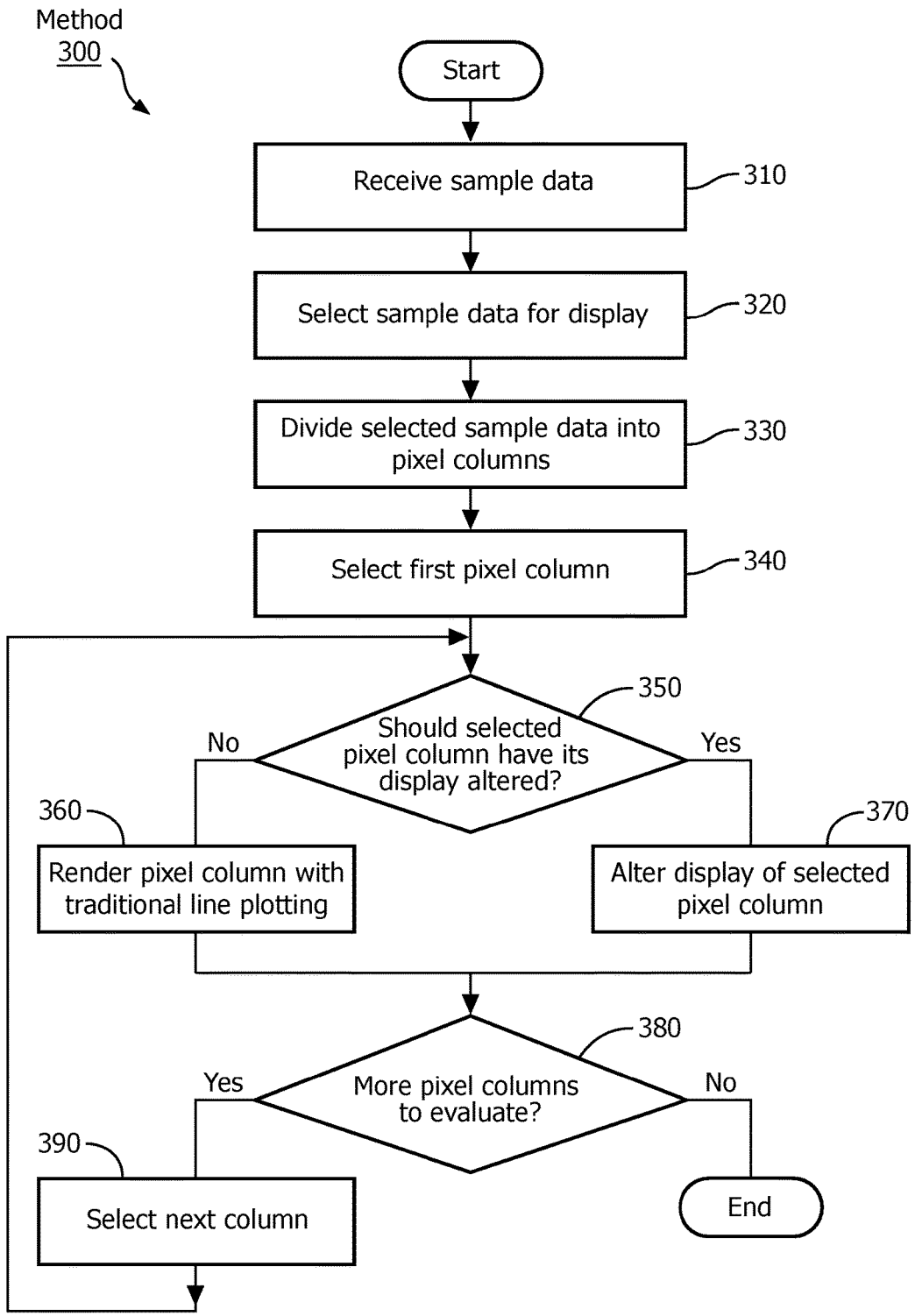
FIG. 3 shows an exemplary method providing for display of the data sample of FIG. 1 in a manner that enhances readability.

FIG. 3 illustrates a method 300 according to an exemplary embodiment. In step 310, sample data is received. Data may be received from any source (e.g., directly from patient monitoring equipment, from a data archive, etc.) and may be in real-time (e.g., received as it is measured) or at any other time. In step 320, a selection, such as the selection shown in FIG. 1, is selected for display. Selection may be manual (e.g., a clinician may select a time interval of interest for a patient) or automated (e.g., a patient's bedside display may automatically select the immediately preceding 24 hour time interval).

In step 330, the selection of sample data made in step 320 is divided into pixel columns. As described above, the division may depend on the number of samples included in the selection and the width of the display to be used in pixels.

For example, continuing with the discussion of one day of data sampled at 1 Hz is shown on a display that is 1920 pixels wide, each pixel column will include $8.64*10^4/1920=45$ samples. Thus, the first pixel column will include the first 45 samples, the second pixel column will include the next 45 samples, etc. It should be noted that this is only exemplary and signals may also be irregularly sampled, meaning that there may be a variable number of samples per pixel column. The irregular sampling may be the results of various factors such as missing data, an irregular sampling scheme, etc. The pixel columns may be considered as time bins, each of which contains a plurality of samples.

In steps 340-390, each pixel column is evaluated to determine whether its display should be altered to improve readability. In step 340, a first pixel column is selected. Typically, this may begin at the left side of a display, which may correspond to the earliest samples chronologically, but any other starting point may also be used.

In step 350, the selected pixel column is evaluated to determine whether its display should be altered. In a first exemplary embodiment, this determination may be made solely based on the number of samples contained within the pixel column. If the number of samples included in the column is greater than a threshold value, display of the pixel column is altered. The threshold value may be, for example, two. This threshold value may be used because if there are two samples within a pixel column, a line drawn between the first and the second will show both samples within the pixel column, but if there are three or more samples within a pixel column, each subsequent sample past the second will not be specifically shown in a line drawn between the highest and lowest sample value. However, for evenly distributed sample selections, wherein each pixel column includes the same number of samples, a determination based solely on the number of samples within a pixel column will result in the entire display either being altered for improved readability or not being altered.

In a second exemplary embodiment, the determination whether to alter the display is based on both the number of samples within the pixel column and the range of values included within the pixel column. In such an embodiment, the display of the selected pixel column is altered if the number of samples within the pixel column exceeds a threshold number, as described above, and if the range of values exceeds a threshold range. Range may be determined as the absolute value of the difference between the maximum value included in the pixel column and the minimum value included in the pixel column. The threshold range to which the range of the selected pixel column is compared may be static (e.g., for a heart rate monitor the threshold range may always be 40 beats per minute) or dynamically determined (e.g., the threshold range may be 20% of the entire range represented by the vertical axis).

If, in step 350, it is determined that the selected pixel column should not have its display altered, then in step 360 the selected pixel column is rendered with traditional line plotting. However, if, in step 350, it is determined that the selected pixel column should have its display altered, then in step 370 the selected pixel column is rendered using an alternative technique to enhance readability. A variety of techniques may be used to accomplish this enhancement.

Figure 4:
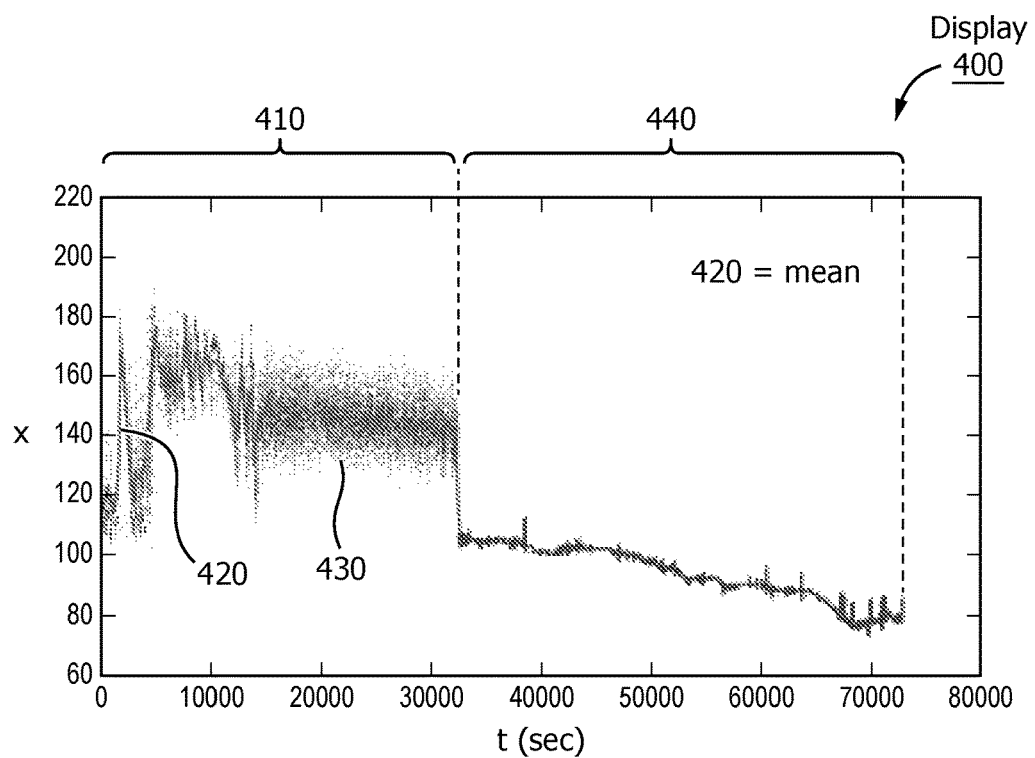
FIG. 4 shows a display of the data sample of FIG. 1 generated according to the exemplary method of FIG. 3.

In one exemplary embodiment, a line histogram may be used in place of traditional line plotting. In such an embodiment, a histogram of all values within the pixel column is generated and plotted along the pixel column. FIG. 4 illustrates a display 400 showing the same data set as shown in FIG. 1, plotted using a line histogram for selected data. Based on the size of the ranges between minimum and maximum values for each pixel column, line histograms are used for samples up to approximately t=33000 seconds, and line plotting is used subsequently. In region 410 of the display 400, black line 420 connects the mean value of each pixel column for which line histograms are used. Gray points 430 clustered around black line 420 represent various samples, with the darkness of the gray corresponding to the frequency of the value within the sample. Region 440 includes samples connected with linear interpolation, as described above. It will be apparent to those of skill in the art that the display 400, and, particularly, the contents of region 410, provides more information than the display 100, and, more specifically, indicates that most values are concentrated around the line 420 indicating the mean, contrary to what the display 100 would suggest.

Figure 5:
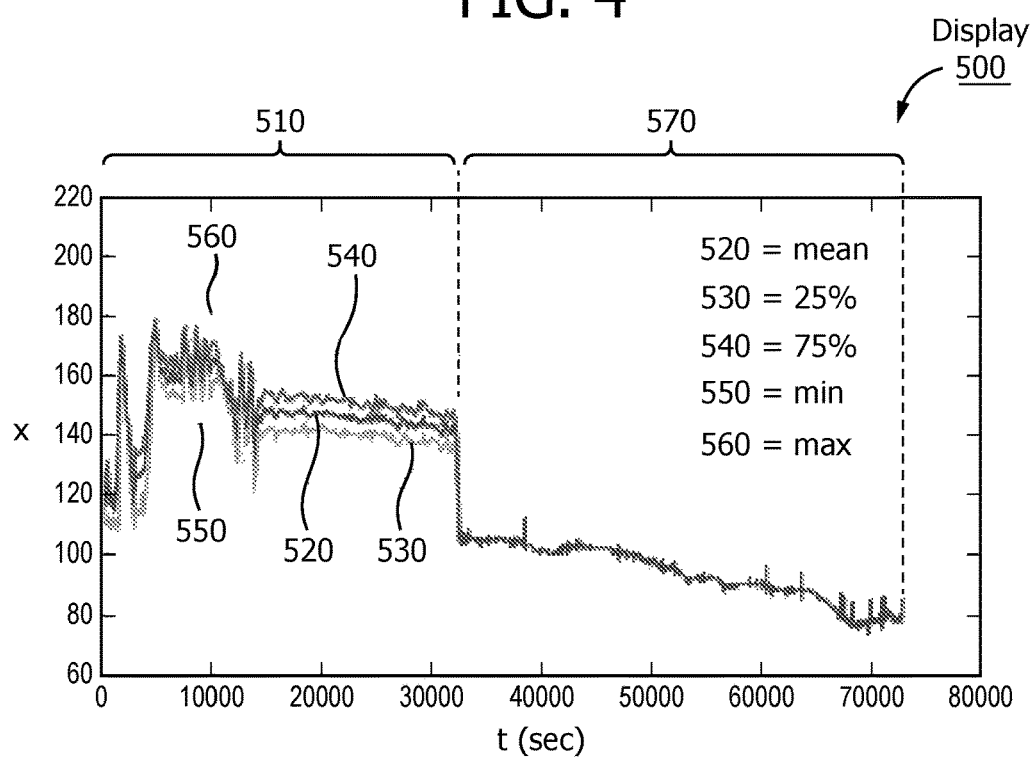
FIG. 5 shows a display of the data sample of FIG. 1 generated according to an alternative version of the exemplary method of FIG. 3.

In another embodiment, the alternative display may take the form of selective display of mean and quantiles. FIG. 5 illustrates such a display 500. In region 510, the display 500 includes a first line 520 indicating the mean of the sample, a second line 530 indicating the 25% quantile of the sample, a third line 540 indicting the 75% quantile of the sample, a cluster of points 550 indicating minimum values, and a cluster of points 560 indicating maximum values. In region 570, linear interpolation is primarily used, though minima and maxima are shown occasionally. The display 500 may give the viewer additional detail regarding the sample. It should be noted that the two examples provided above of alternative displays are only exemplary and there may be other alternative manners of displaying the data.

In step 380, it is determined whether there are more pixel columns to be evaluated. If more pixel columns need to be evaluated, then, in step 390, the next pixel column is selected. After step 390, the method 300 returns to step 350, and the evaluation of pixel columns continues. If no more pixel columns need to be evaluated, then the plot is complete and the method 300 ends.

Figure 6:
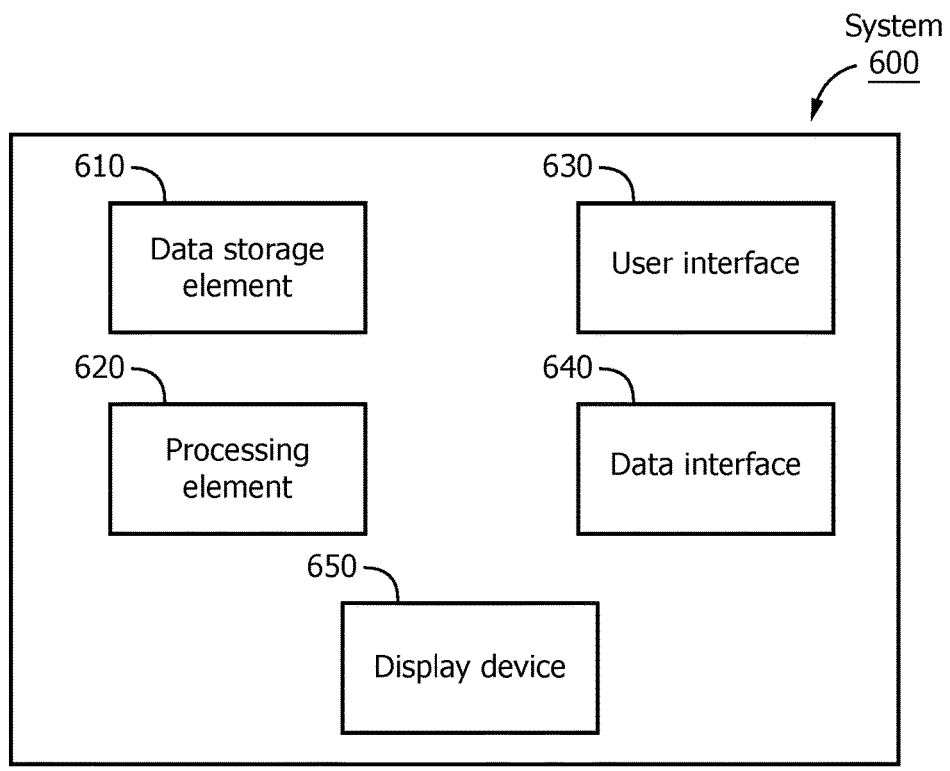
FIG. 6 shows an exemplary computing system that implement the exemplary method of FIG. 3.

FIG. 6 illustrates an exemplary system 600 that may implement the exemplary embodiments described above with reference to method 300. The system 600 includes a data storage element 610 (e.g., one or more hard drives, solid state drives, or other persistent data storage components). The data storage element 610 may store code for implementing the method 300. The system 600 also includes a processing element 620, which may include one or more microprocessors capable of executing code such as the code for implementing the method 300. The system 600 also includes a user interface 630, which may comprise one or more physical components (e.g., a keyboard, mouse, touchpad, display, touchscreen, etc.) operable to receive user inputs and provide results (e.g., the display 400) to a user. The system 600 also includes a data interface 640 (e.g., a wired or wireless connection to a network and/or to the Internet) providing for communications (e.g., receipt of sample data in step 310) with external data sources. The system 600 also includes a display device 650 (e.g., a LCD display, and LED display, a CRT display, etc.) It should be noted that in some implementations the display device 650 and the user interface 630 may be a single integrated device (e.g., a touchscreen that both displays information and receives input from the user). It should also be noted that it is possible that the display device 650 is a separate component from the system 600. That is, the system 600 may process the data as described with respect to the method 300 for display on a separate display device 650. It will be apparent to those of skill in the art that there may be any number of possible implementations of a system 600, that such implementations may include additional elements not specifically described above, and that the system 600 may be capable of performing additional tasks beyond those described above with reference to the exemplary embodiments.

Figure 7:
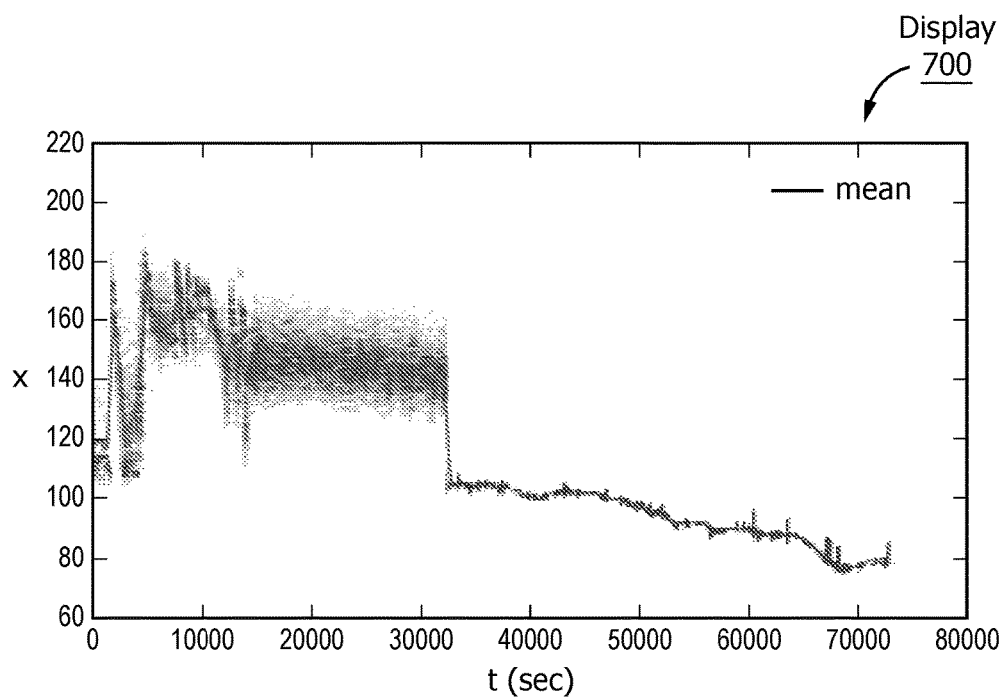
FIG. 7 shows a display of the data sample of FIG. 1 generated according to an alternative version of the exemplary method of FIG. 3.

In an alternative embodiment, rather than using pixel columns, a different width can be used as the basis of evaluation. The width may be defined based on a greater number of pixels or a portion of the scale represented by the horizontal axis. A different width may be selected based on a typical viewing distance from the user to the screen; for example, where the typical viewing distance is further away from the screen, it may be desirable to use a greater width as the basis of evaluation. Alternatively, where larger sample markers are used (e.g., "x" or "o"), it may be desirable to use a greater width. FIG. 7 illustrates a display 700 that generates histograms based on larger time windows of consideration. As will be apparent, the use of larger time windows results in a smoother histogram.

In another alternative embodiment, rather than using a histogram for regions of a plot where alternative display is desired, a more advanced distribution estimator may be used. This may be, for example, a kernel density estimation or a parametric estimate of the distribution function. Alternatively, for near-periodic signals (e.g., electrocardiogram signals or photoplethismograph signals), dense areas of the sample can be summarized using a plot of the average signal per period, which may also include an indication of signal variation. A larger time interval of dense data (e.g., data for which alternative display is desired) may be required to allow for such a 2-D summarizing plot.

In a further exemplary embodiment, the alternative display may be used to display 2-D scatterplots. In this example, each pixel may be a histogram or single pixel. A different color can be used for the histogram notation to distinguish the two representations. For example, if the pixel represents a histogram of data points, the pixel may be displayed in blue, whereas if the pixel represents a single data point in the scatterplot, the pixel may be displayed in red.

The exemplary embodiments described above have made specific reference to display of time series, wherein a plot includes sample values plotted along the y-axis at time values along the x-axis. However, it will be apparent to those of skill in the art that time series are only one type of data, and that the exemplary embodiments are equally applicable to the display of any type of data sample in an (x, y) format.

The exemplary embodiments described above may improve the readability and utility of a plot containing a densely packed sample of data. Because a plot using standard linear interpolation becomes difficult to read for such densely packed samples, as described above with reference to FIG. 1, the selective use of a histogram, as shown in FIG. 4, enables the viewer to obtain more information than such a standard plot. Further, the selective use of a histogram presents an advantage over a plot that exclusively uses a histogram for all data, because for sparse data samples linear interpolation provides a visual aid to the observer to correctly interpret the signal.

Those of skill in the art will understand that the above-described exemplary embodiments may be implemented in any number of matters, including as a software module, as a combination of hardware and software, etc. For example, the exemplary method 300 may be embodied in a program stored in a non-transitory storage medium and containing lines of code that, when compiled, may be executed by a processor.

It will be apparent to those skilled in the art that various modifications may be made to the exemplary embodiments, without departing from the spirit or the scope of the invention. Thus, it is intended that the present invention cover modifications and variations of this invention provided they come within the scope of the appended claims and their equivalents.

What is claimed is:

1. A non-transitory computer-readable storage medium storing a set of instructions that are executable by a processor, the set of instructions, when executed by the processor, causing the processor to perform operations comprising:

receiving data including a plurality of data points, each of the data points including a value along a first axis and a value along a second axis;

dividing the data into a plurality of bins along the first axis, wherein the data is divided based on a number of pixel rows or columns of a display device on which the data is to be displayed;

determining, for one of the bins, whether an alternative data representation should be used, wherein the determining is based on a number of data points within the one of the bins, and wherein the alternative data representation is used in one of the bins when the number of data points in the one of the bins is greater than a first threshold; and displaying a plot of the data, wherein the alternative data representation is used for the one of the bins when it is determined that the alternative data representation should be used, wherein line plotting is used for the one of the bins when it is determined that the alternative data representation should not be used, wherein the alternative data representation comprises a line histogram, a first line indicating a mean of values along the second axis for the data points in the one of the bins and a second line indicating a quantile of the values along the second axis for the data points in the one of the bins, a kernel density estimation of the data, a parametric estimate of a distribution function of the data, or an average signal per period for near periodic data.

2. The non-transitory computer-readable storage medium of claim 1, wherein the determining is further based on a range of values along the second axis for the data points within the one of the bins.

3. The non-transitory computer-readable storage medium of claim 2, wherein the alternative data representation is used in one of the bins when both A) the number of data points in the one of the bins is greater than a first threshold, and B) the range of values along the second axis in the one of the bins is greater than a second threshold.

4. The non-transitory computer-readable storage medium of claim 1, wherein each pixel column of the display device is used to display data points of a corresponding bin of the plurality of bins.

5. The non-transitory computer-readable storage medium of claim 1, wherein the alternative data representation comprises a line histogram.

6. The non-transitory computer-readable storage medium of claim 5, wherein the line histogram comprises a mean of values for the data points in the one of the bins.

7. A system, comprising:
a data interface receiving data including a plurality of data points, each of the data points including a value along a first axis and a value along a second axis;
a display device;
a non-transitory memory storing a set of instructions; and
a processor executing the set of instructions to perform operations including:
dividing the data into a plurality of bins along the first axis, wherein the data is divided based on a physical attribute of the display device;
determining, for one of the bins, whether an alternative data representation should be used, wherein the determining is based on a number of data points within the one of the bins, and wherein the alternative data representation is used in one of the bins when the number of data points in the one of the bins is greater than a first threshold; and
displaying, using the display device, a plot of the sample of data, wherein the alternative data representation is used for the one of the bins when it is determined that the alternative data representation should be used, wherein line plotting is used for the one of the bins when it is determined that the alternative data representation should not be used,
wherein the alternative data representation comprises a line histogram, a kernel density estimation of the data, a parametric estimate of a distribution function of the data, or an average signal per period for near periodic data.

8. The system of claim 7, wherein the determining is further based on a range of values for the data points within the one of the bins.

9. The system of claim 8, wherein the alternative data representation is used in one of the bins when both A) the number of data points in the one of the bins is greater than a first threshold, and B) the range of values in the one of the bins is greater than a second threshold.

10. The system of claim 7, wherein each of the bins comprises a number of pixel columns of the display device.

11. The system of claim 7, wherein the alternative data representation comprises a line histogram.

12. The system of claim 7, wherein the alternative data representation comprises a first line indicating a mean of values for the data points in the one of the bins and a second line indicating a quantile of the values for the data points in the one of the bins.

13. The system of claim 7, wherein the alternative data representation comprises one of a kernel density estimation of the data, a parametric estimate of a distribution function of the data, or an average signal per period for near periodic data.

14. A method for controlling a display device, comprising:
receiving data including a plurality of data points, each of the data points including a chronological value along a chronological axis and a sample value along a sample axis;
dividing the data into a plurality of bins along the chronological axis, wherein the data is divided based on a physical attribute of a display device on which the data is to be displayed;
determining whether the data points are to be displayed using a first data representation or a second data representation, wherein the determining is based on a number of data points within the one of the bins; and
displaying a plot of the data wherein a histogram representation of the data points of a given bin of the plurality of bins are displayed plotted along a pixel row or column parallel to the sample axis when it is determined the first data representation is to be used, and the second type of representation of at least some of the data points is displayed when it is determined the second data representation is to be used.

* * * * *